United States Patent

Ajello et al.

[11] Patent Number: 5,922,249
[45] Date of Patent: Jul. 13, 1999

[54] OPHTHALMIC LENS PRODUCTION PROCESS

[75] Inventors: Ellen Marie Ajello, Decatur, Ga.; Dieter Lohmann, Munchestein, Switzerland; Jens Hopken; Angelika Domschke, both of Lorrach, Germany

[73] Assignee: Novartis AG, Basel, Switzerland

[21] Appl. No.: 08/944,940

[22] Filed: Oct. 2, 1997

Related U.S. Application Data

[63] Continuation-in-part of application No. 08/911,571, Aug. 14, 1997, and application No. 08/569,816, Dec. 8, 1995, Pat. No. 5,760,100.

[51] Int. Cl.$^6$ .................................................. B29D 11/00
[52] U.S. Cl. ............................ 264/1.1; 95/43; 264/85; 425/808
[58] Field of Search ........................... 264/1.1, 85, 101, 264/102; 95/47, 54, 43, 53; 425/808

[56] References Cited

U.S. PATENT DOCUMENTS

| | | | |
|---|---|---|---|
| 2,542,386 | 2/1951 | Beattie . | |
| 3,551,541 | 12/1970 | Rossetti . | |
| 3,621,892 | 11/1971 | Gillespie . | |
| 3,894,024 | 7/1975 | Cherenko et al. | 264/331 |
| 4,054,624 | 10/1977 | Boeuf . | |
| 4,057,376 | 11/1977 | Berger | 425/73 |
| 4,234,533 | 11/1980 | Langlands | 264/261 |
| 4,342,723 | 8/1982 | Sado | 422/48 |
| 4,386,039 | 5/1983 | Szycher | 264/1.1 |
| 4,495,313 | 1/1985 | Larsen | 523/106 |
| 4,578,455 | 3/1986 | Pipper et al. | 528/501 |
| 4,640,489 | 2/1987 | Larsen | 249/122 |
| 4,680,336 | 7/1987 | Larsen . | |
| 4,711,647 | 12/1987 | Guthmann . | |
| 4,729,773 | 3/1988 | Shiato . | |
| 4,786,444 | 11/1988 | Hwang | 264/85 |
| 4,889,664 | 12/1989 | Kindt-Larsen et al. | 264/2.6 |
| 5,039,459 | 8/1991 | Kindt-Larsen et al. | 264/2.6 |
| 5,080,839 | 1/1992 | Kindt-Larsen et al. | 264/2.6 |
| 5,094,609 | 3/1992 | Kindt-Larsen et al. | 425/445 |
| 5,106,930 | 4/1992 | Gupta | 526/251 |
| 5,123,937 | 6/1992 | Shihata et al. . | |
| 5,130,070 | 7/1992 | Martin | 264/102 |
| 5,222,118 | 6/1993 | Gerth | 378/200 |
| 5,260,001 | 11/1993 | Nandu et al. | 264/2.1 |
| 5,425,803 | 6/1995 | Schravendijk et al. | 95/46 |
| 5,435,943 | 7/1995 | Adams et al. | 264/1.1 |
| 5,522,917 | 6/1996 | Honda | 95/46 |
| 5,656,208 | 8/1997 | Martin et al. | 264/1.1 |

FOREIGN PATENT DOCUMENTS

WO9631972 12/1995 WIPO .

*Primary Examiner*—Mathieu D. Vargot
*Attorney, Agent, or Firm*—Michael U. Lee

[57] ABSTRACT

A method of making an ophthalmic lens including the steps of: preparing a polymerizable composition comprising excessive oxygen content; contacting the polymerizable composition with a gas that is inert or substantially inert to the polymerizable composition, and deoxygenating or partially deoxygenating the polymerizable composition; conveying all or part of the polymerizable composition to an ophthalmic lens mold; polymerizing all or part of the polymerizable composition and obtaining a polymeric ophthalmic lens, and the lens produced by such process.

30 Claims, 2 Drawing Sheets

OPHTHALMIC LENS PRODUCTION PROCESS

RELATED APPLICATIONS

This application is a continuation in part of U.S. Ser. No. 08/911,571, filed Aug. 14, 1997 and a continuation in part of U.S. Ser. No. 08/569,816, filed Dec. 8, 1995, now U.S. Pat. No. 5,760,100.

FIELD OF THE INVENTION

This invention relates generally to processes for producing ophthalmic lenses, and to methods of deoxygenating ophthalmic lens polymerizable compositions in such production processes.

BACKGROUND OF THE INVENTION

Ophthalmic lenses are produced by several known processes, including spin casting, precision lathing, and molding. In spin casting processes a suitable ophthalmic lens composition is concurrently rotated and polymerized in a mold, as described generally by Nandu et al. in U.S. Pat. No. 5,260,001. Precision lathing is performed by lathing a piece of clear polymeric material into the shape of a lens, and polishing the lens thus formed. Precision lathing is described generally by Le Boeuf et al. in U.S. Pat. No. 4,054,624. Molding operations are carried out by polymerizing a suitable material in a preformed mold, as described generally by Larsen in U.S. Pat. No. 4,640,489.

Various compositions are used to manufacture ophthalmic lenses. The composition chosen for a particular application depends upon the physical and optical properties of the lens that one is attempting to obtain, as well as the type of process used to manufacture the lens and the particular processing conditions associated with such process. A particularly popular type of ophthalmic lens is the soft contact lens, which is made from compositions that are hydrophilic, and thus absorb water. Exemplary hydrophilic lenses are based upon polymers and copolymers of 2-hydroxyethylmethacrylate.

A soft contact lens that is gaining wide acceptance is the extended wear lens, which people can keep on the cornea surface overnight, and for periods of time exceeding seven days. Extended wear lenses must meet special physical criteria because the cornea relies for oxygen upon diffusion from the ambient air, and a contact lens is a physical barrier to such diffusion. To overcome this physical barrier, manufacturers have developed special oxygen permeable compositions for extended wear lenses. Such oxygen permeable compositions generally contain elements or compounds that attract oxygen, such as silicon and fluorine. A variety of siloxane-containing polymers having high oxygen permeability are described, for example, in U.S. Pat. Nos. 3,228,741, 3,341,490, 3,996,187, and 3,996,189.

Ophthalmic lenses are often produced from compositions that include a volatile component such as a solvent or diluent. For example, many ophthalmic lenses are manufactured from polymerizable compositions in which the monomeric component(s) are solubilized in an appropriate solvent. Many ophthalmic lenses are manufactured with carrier volatile components, which are extracted from the lenses after polymerization and replaced with water. Whenever volatile components are included in ophthalmic lens compositions, extreme care must be taken to prevent evaporation of the volatile component(s), which can alter the ratio of ingredients in the composition. To minimize the risk of evaporation, exposure to ambient gasses is minimized, and excessive turbulence is also minimized.

Ophthalmic lenses must meet very demanding standards. As previously noted, extended wear lenses must be sufficiently hydrophilic and permeable to oxygen. In addition, ophthalmic lenses must be strong enough to withstand tearing, and they must meet demanding dimensional requirements to achieve the prescribed optical correction, and to match the corneal dimensions of the wearer. Moreover, the lens must be extremely thin, to facilitate oxygen permeability, and to enhance the comfort to the wearer. The lens must also be clear and without distortion, to provide pleasing and precise optical correction. Processing conditions that can meet the stringent lens standards are very demanding, and manufacturers establish rigorous quality control programs, and continuously evaluate and revise their operating procedures, to minimize the incidences of defective lenses.

A major concern in any quality control program is contamination, including contamination from ambient gasses. In the process of preparing polymerizable compositions, the various ingredients can be exposed to ambient gasses, which are absorbed by the ingredient(s) and contaminate the polymerizable composition. Absorbed gasses such as oxygen interfere with the lens production process by quenching free radicals produced during polymerization. Gasses can also react with the polymer components to produce undesirable by-products. Absorbed gasses also can cause bubbles in the polymerized ophthalmic lens, which severely compromise the optical and mechanical integrity of the lens.

Recent advances in ophthalmic lens compositions and polymerization technologies have dictated corresponding advances in the removal of dissolved contaminants, such as gasses, from the ophthalmic lens composition. Ophthalmic lenses that are being manufactured and developed today are much more sensitive to gaseous contamination than the ophthalmic lenses that were developed just a few years ago. Methods have, accordingly, been developed to remove nearly all dissolved gasses from the polymerizable composition. These methods minimize the risk of solvent volatilization, while maximizing the removal of gasses.

U.S. Pat. No. 5,453,943 to Adams et al., for example, discloses a process that produces a composition having an oxygen concentration of less than 1 part per million. The composition is passed through a selectively porous tubing which, when exposed to a vacuum, draws the gasses from the composition through the tubing. The 943 patent teaches the removal of all dissolved gasses from the composition. Moreover, the 943 patent dictates a strong preference for silicon tubing, apparently because of silicon s strong affinity for oxygen, which allows the tubing to draw oxygen from polymerizable compositions that also have a high affinity for the oxygen. The process of the 943 process suffers, however, from its complexity and time requirements. The polymerizable composition must be drawn through over 60 meters of tubing, and is deoxygenated at a rate of only 8.5 ml./minute.

It was surprising to find, therefore, that quality ophthalmic lenses could be manufactured by a process in which the composition is deoxygenated by bubbling an inert gas such as nitrogen through the composition. Inert gas bubbling surprisingly deoxygenates the polymerizable composition in such a short time period, and under such light flow conditions, that only a minimal quantity of solvent evaporates. Light inert gas bubbling virtually eliminates oxygen content from ophthalmic lens compositions, in less than one twentieth of the time required by the porous tubing process disclosed by U.S. Pat. No. 5,453,943 (see Table 3), even for polymerizable compositions that exhibit a strong affinity for the oxygen.

Moreover, the process is effective even though it merely replaces one dissolved gas, oxygen, with another dissolved gas such as, for example, nitrogen. Lenses produced with compositions that are saturated with inert gas from the bubbling process are statistically indifferent from prior art lenses in which both nitrogen and oxygen are removed.

SUMMARY OF THE INVENTION

In accordance with the purpose(s) of this invention, as embodied and broadly described herein, this invention, in one aspect, relates to a method of making an ophthalmic lens comprising the steps of preparing a polymerizable composition comprising excessive oxygen content; contacting the polymerizable composition with a gas that is inert or substantially inert to the polymerizable composition, and deoxygenating or partially deoxygenating the polymerizable composition; conveying all or part of the polymerizable composition to an ophthalmic lens mold; polymerizing all or part of the polymerizable composition and obtaining a polymeric ophthalmic lens. The invention further provides an ophthalmic lens produced by such process.

In another aspect the invention relates to an ophthalmic lens polymerizable composition that is saturated or substantially saturated with an inert gas.

In another aspect the invention relates to an ophthalmic lens prepared from an ophthalmic lens polymerizable composition that is saturated or substantially saturated with an inert gas.

In yet another aspect the invention relates to an ophthalmic lens that is saturated or substantially saturated with an inert gas.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1:
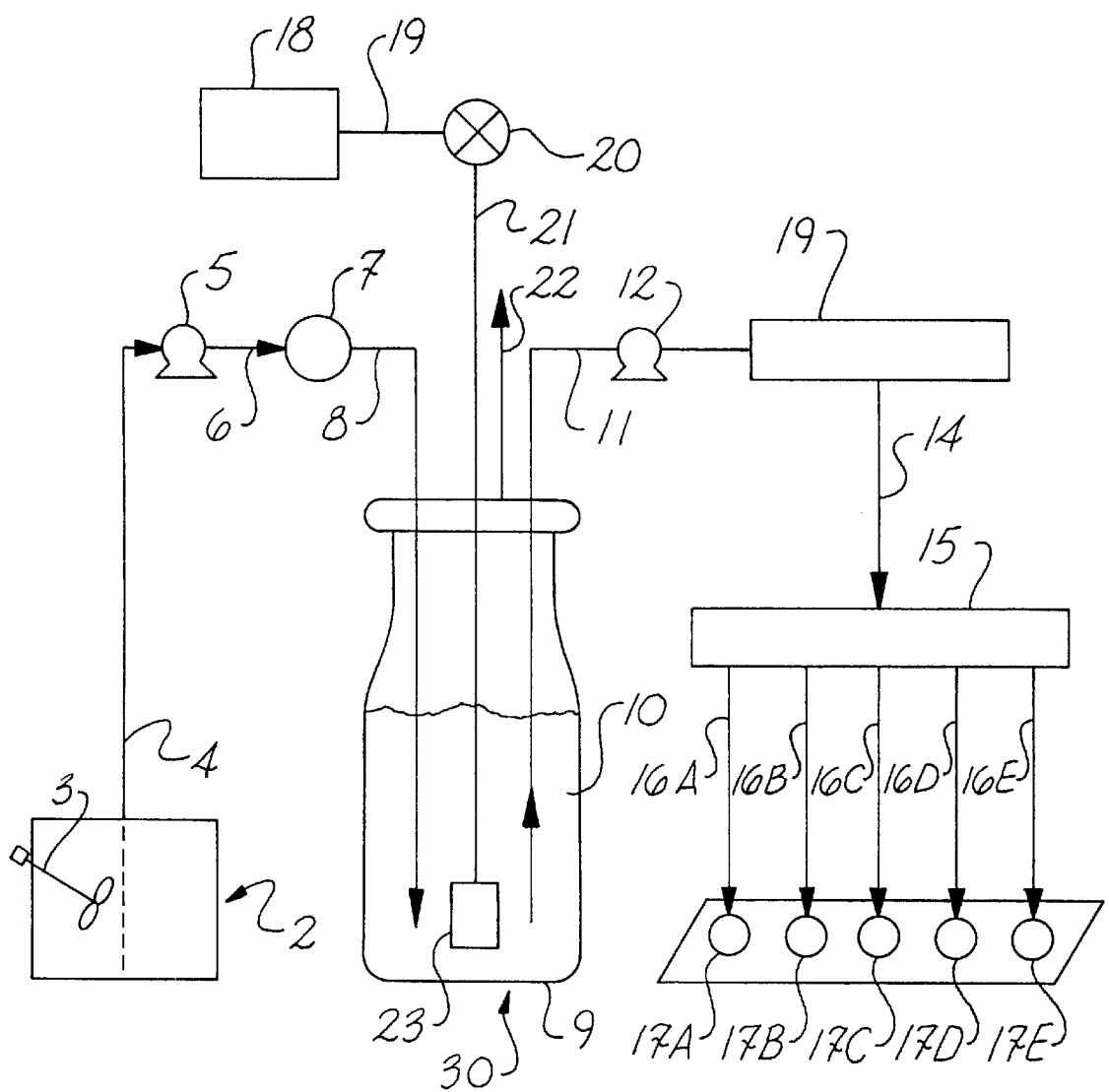
FIG. 1 is a simplified flow chart showing the various components of a lens production process, including a deoxygenating unit.

The present invention may be understood more readily by reference to the following detailed description of preferred embodiments of the invention and the Examples included therein and to the Figures and their previous and following description. Before the present compounds, compositions and methods are disclosed and described, however, it is to be understood that this invention is not limited to specific production processes, or to particular ophthalmic lens formulations, as such may, of course, vary. It is also to be understood that the terminology used herein is for the purpose of describing particular embodiments only and is not intended to be limiting.

DEFINITIONS

In this specification and in the claims which follow, reference will be made to a number of terms which shall be defined to have the following meanings:

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

"Excessive oxygen content" in a polymerizable composition means a level of oxygen that materially interferes with the free radical polymerization of the composition, or that materially affects the quality, properties, or composition of an ophthalmic lens obtained upon polymerization of the composition.

Hydrophilic describes a polymer that will more readily associate with water than with lipids. A hydrophilic enhancing prepolymer means a prepolymer that polymerizes to form a hydrophilic polymer.

Macromer refers to a polymerizable material that has a molecular weight of at least about 800 grams per mole. The term macromer also encompasses oligomers.

Material means greater than de minimis, and excludes those amounts of a particular property or physical characteristic in, for example, a polymerizable composition, that are generally within quality control specifications and guidelines recognized by workers of ordinary skill in the art, and that do not interfere with the processes of the invention or otherwise give rise to unacceptable results or ophthalmic lenses when practicing the process of the invention, again as determined by quality control specifications and guidelines recognized by workers of ordinary skill in the art.

Monomer refers to a polymerizable material that has a molecular weight of less than about 800 grams per mole. "Ophthalmic lens" refers to lenses that are placed in intimate contact with the eye or tear fluid, such as contact lenses for vision correction (e.g., spherical, toric, bifocal), contact lenses for modification of eye color, ophthalmic drug delivery devices, ocular tissue protective devices (e.g., ophthalmic healing promoting lenses), and the like.

The terms "optional" and "optionally" mean that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

Oxygen permeable describes a polymer through which oxygen can permeate. An oxygen permeability enhancing prepolymer means a prepolymer that polymerizes to form an oxygen permeable polymer.

Parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A polymerizable composition means a composition that contain one or more prepolymers, such as monomers, oligomers, macromers and other units that are capable of polymerization, and mixtures thereof.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH CH O— units in the polyester, regardless of whether ethylene glycol was used to prepare the polyester. Similarly, a siloxy residue in a composition refers to the silicon moiety within the composition, whether the silicon moiety is obtained directly from elemental silicon or a compound that contains silicon.

TRIS refers to 3-methacryl oxypropyltris (trimethylsiloxy) silane, which is represented by CAS No. 17096-07-0. The term TRIS also includes dimers of 3-methacryl oxypropyltris (trimethylsiloxy) silane.

The term "volatile" often describes a component of a polymerizable composition, and in such context describes a degree of volatility that would lead a worker of skill in the art to expect greater than de minimis volatilization when the polymerizable composition is processed according to the process of this invention. A "de minimis" amount of volatilization means less than a material amount of volatilization. The term de minimis can take into account the particular system employed. Thus, in a system that returns volatilized solvent to the polymerizable composition, a "de minimis" amount of volatilization would be greater than in a system that does not return the volatilized solvent to the composition.

It must be noted that, as used in the specification and the appended claims, the singular forms "a," "an" and "the" include plural referents unless the context clearly dictates otherwise. Thus, for example, reference to "a hydrophilic enhancing prepolymer" includes mixtures of hydrophilic enhancing prepolymers, reference to "a volatile carrier" includes mixtures of two or more such carriers, and the like.

Moreover, ranges are often expressed herein as from about one particular value, and/or to about another particular value. When such a range is expressed, it is to be understood that a more preferred range is typically from the one particular value and/or to the other particular value. Similarly, when values are expressed as approximations, by use of the antecedent about, it will be understood that the particular value is typically more preferred.

DISCUSSION

In one aspect the invention provides a method of making an ophthalmic lens comprising the steps of: preparing a polymerizable composition comprising excessive oxygen content; contacting the polymerizable composition with a gas that is inert or substantially inert to the polymerizable composition, and deoxygenating or partially deoxygenating the polymerizable composition; conveying all or part of the polymerizable composition to an ophthalmic lens mold; and polymerizing all or part of the polymerizable composition and obtaining a polymeric ophthalmic lens.

The polymerizable composition can be prepared by any method known to those skilled in the art, and can comprise any combination of materials that is suitable for preparing ophthalmic lenses. Generally, the composition is prepared by combining the ingredients of the composition in a suitable container, and blending the ingredients until a homogenous mixture is obtained.

The invention is particularly well adapted to processes for producing hydrophilic lenses, and to compositions that are useful for producing such lenses. In a preferred embodiment, therefore, the polymerizable composition contains one or more hydrophilic enhancing prepolymers. A wide range of hydrophilic enhancing prepolymers are known in the art and are suitable for practicing the invention. Preferred hydrophilic enhancing prepolymers are the acrylates and methacrylates, such as 2-hydroxyethyl methacrylate, acrylamide, methacrylamide, and dimethylacrylamide; the poly(alkylene glycols) such as poly(ethylene glycol); the N-vinyl pyrrolidones such as N-vinyl-2-pyrrolidone; and mixtures thereof.

The invention is also particularly well adapted to processes for producing oxygen permeable lenses, and to compositions which, when polymerized, yield such lenses. A wide range of materials may be polymerized to form a polymer having a relatively high oxygen diffusion rate. Preferred oxygen permeability enhancing prepolymers are macromers and monomers containing silicon residues, macromers and monomers containing fluorine residues, alkyne macromers and monomers, and mixtures thereof. Particularly preferred oxygen permeability enhancing prepolymers are macromers that comprise silicon residues. Macromers having dialkylsiloxane groups, especially dimethylsiloxanes, are especially preferred. Macromers that contain dimethylsiloxane oligomeric residues, and polymers that contain dimethylsiloxane residues, are broadly referred to as polydimethylsiloxanes regardless of whether the macromer or polymer also contains other residues.

The polymerizable composition may further comprise a wide variety of other polymerizable materials. Cross-linking agents, such as ethylene glycol dimethacrylate may be added to improve structural integrity and mechanical strength in the polymerized lens. Antimicrobial prepolymers such as poly(quaternary ammonium) salts may be added to inhibit microbial growth on the lens material. Also, additional hydrophilic or oxygen permeable enhancing prepolymers may be added to adjust the oxygen permeability and hydrophilicity of the final molded lens. An especially advantageous polymerizable material is TRIS, which may act both to increase oxygen permeability and to improve the modulus of elasticity.

In a particular embodiment the composition comprises a volatile component, such as a solvent that dissolves and miscibilizes the components of the polymerizable composition. Solvents are particularly useful when oxygen permeability and hydrophilic enhancing prepolymers are both included in the polymerizable composition, due to the immiscibility often experienced when mixing such prepolymers. The volatile component may also be a diluent that upon polymerization is extracted from the lens. The volatile component typically is substantially inert, and does not participate in the polymerization of the composition. The volatile component may, however, be an active ingredient of the composition that participates in the polymerization.

A wide variety of solvents are known that typically are chosen based upon their interaction with the ingredients of the polymerizable composition. Suitable solvents are in principal all solvents which dissolve the components of the composition, for example, water, alcohols, and especially the lower alkanols such as ethanol and methanol. In other embodiments the solvent is an ether, such as tetrahydrofuran, diethyl ether, diethylene glycol dimethyl ether or dioxane; a halogenated hydrocarbon such as chloroform, trichloroethane, or methylene chloride; a bipolar aprotic solvent such as methyl ethyl ketone, acetonitrile, acetone, dimethylformamide or dimethyl sulfoxide; a carboxylic acid amide such as dimethylformamide; a hydrocarbon such as hexane, petroleum either, toluene or xylene; and furthermore pyridine or n-methylmorpholine, and also mixtures of suitable solvents, such as mixtures of alcohol and water.

A preferred polymerizable composition comprises oxygen permeability and hydrophilic enhancing prepolymers. A particularly preferred composition comprises from about 40 to about 80 parts by weight oxygen permeability enhancing prepolymer(s), and from about 10 to about 40 parts by weight hydrophilic enhancing prepolymer(s). A more preferred polymerizable composition comprises from about 60 to about 70 parts by weight oxygen permeability enhancing prepolymer(s), and from about 20 to about 30 parts by weight hydrophilic enhancing prepolymer(s). In an optional embodiment, the composition preferably comprises from about 10 to about 20 wt. % TRIS, and more preferably from about 12 to about 15 wt. % TRIS. In another optional embodiment, the composition preferably comprises from about 5 to about 45 wt. % of the volatile component, more preferably from about 15 to about 35 wt. % of the volatile component, and even more preferably from about 18 to about 30 wt. % of the volatile component, and still even more preferably from about 20 to about 23 wt. % of the volatile component. Preferred compositions also are set forth in the specifications of U.S. Ser. No. 60/027,736, and PCT/EP96/01265, the disclosures from which being hereby incorporated by reference.

It has been surprisingly found that the invention can be practiced with polymerizable compositions that comprise a volatile component, even polymerizable compositions that are sensitive to the loss of volatile component from the composition. For example, the invention surprisingly can be performed with compositions that have a range over which the weight of the volatile component concentration can vary, without materially affecting the lens obtained upon polymerization, of less than about 10% (based upon the weight percentage of the component in the composition), even less than about 5%, and even more surprisingly less than about 3%. Moreover, the invention can be practiced with polymerizable compositions regardless of the volatility of the component. The invention can, for example, surprisingly be practiced with compositions in which the volatile component has a vapor pressure in excess of 20 mm Hg at 20 C, with compositions in which the volatile component has a vapor pressure in excess of 40 mm Hg at 20 C, and even with compositions in which the volatile component has a vapor pressure in excess of 60 mm Hg at 20 C.

If the polymerization of the composition is to be initiated by photopolymerization, it may be appropriate to add a photoinitiator that can initiate free radical polymerization and/or cross linking. Examples thereof are customary to the persons skilled in the art. Particularly suitable photoinitiators are benzoinmethylether, 1-hydroxycyclohexylphenyl ketone, Darocur and Irgacur products, preferably Darocur 1173 and Irgacur 2959. Reactive photoinitiators may also be employed which can, for example, be incorporated into a macromer, or be used as a specific comonomer. Particularly suitable examples thereof are given in European Patent No. 0632329, the disclosure from which being hereby incorporated by reference.

The invention is especially well adapted to processes for producing extended wear ophthalmic lenses that are both hydrophilic and oxygen permeable. Compositions used to produce such lenses often contain insoluble hydrophilic and oxygen permeable enhancing prepolymers, that can only be solubilized with the aid of a solvent. Such compositions also are often very sensitive to variations in the ratios of the components, due to the precise ratio of ingredients that must be observed to obtain a polymer that is both hydrophilic and oxygen permeable, and the likelihood of solvent volatilization from such compositions.

Preferably, the process produces a contact lens having a Dk/t of at least 70 barrers/mm and an Ionoton Ion Permeability Coefficient of at least $0.2 \times 10^{-6}$ cm$^2$/sec. More preferably, the process produces a contact lens having a Dk/t of at least 75 barrers/mm and an Ionoton Ion Permeability Coefficient of at least $0.3 \times 10^{-6}$ cm$^2$/sec. The process even more preferably provides a contact lens having a Dk/t of at least 87 barrers/mm and an Ionoton Ion Permeability Coefficient of at least $0.4 \times 10^{-6}$ cm$^2$/sec.

The invention is particularly applicable to processes in which the surface tension and viscosity of the polymerizable composition are low. In a preferred embodiment, therefore, the polymerizable composition has a surface tension below about 250 dynes/cm, even more preferably below about 150 dynes/cm, even further preferably below about 75 dynes/cm, still even more preferably below about 35 dynes/cm, and in an even still more preferred embodiment the surface tension is below about 23 dynes/cm. The surface tension generally will exceed about 10 dynes/cm. In another preferred embodiment the viscosity of the polymerizable composition is below about 3000 cps at 20 C. In an even more preferred embodiment the viscosity is below about 750 cps at 20 C, still even more preferably below about 150 cps at 20 C, even further preferably below about 75 cps at 20 C, and in still an even further preferred embodiment the viscosity of the composition is below about 30 cps at 20 C. The viscosity typically exceeds about 15 cps at 20 C.

Additional details of the process are contained in the drawings and the discussion of the drawings that follows.

A schematic diagram of an exemplary manufacturing process 1 is shown in FIG. 1. In FIG. 1 the composition is first prepared by combining the ingredients of the composition in a container 2, and mixing the ingredients with an impeller 3. The mixing is not, of course necessary. Moreover, it could be accomplished by other means known to workers skilled in the art, such as by agitation and static mixing. Moreover, the polymerizable composition could be prepared in a different location from the rest of the process, or in another manner disconnected from the rest of the process, and still be within the scope of the invention. In the process of FIG. 1, however, after the composition has been prepared it is pumped from container 2 through line 4, by pump 5, through line 6, to a filtration unit 7 where impurities such as particulates in the composition are removed. The material used in line 4, in addition to other lines in the process, are made from any gas impermeable material with which the composition is not chemically reactive. After filtration the composition is fed, via line 8, into container 9 of inert gas sparging unit 30.

In a continuous process the composition is fed continuously into an existing charge 10 of polymerizable composition located in container 9, whereas in a batch operation the charge 10 is depleted and restored with each batch. Regardless of whether the process is continuous or batch, however, charge 10 is deoxygenated by contacting an inert gas with the composition. In FIG. 1 inert gas sparging unit 30 comprises a source of inert gas 18, fed through line 19, valve 20, line 21, and porous frit 23, into charge 10. The source of inert gas 18 preferably is under pressure so that actuation of valve 20 regulates, releases, and stops the flow of inert gas into charge 10. The inert gas could, however, also be supplied by a pump.

When inert gas is fed through line 21 it is dissipated through porous frit 23 into charge 10. The inert gas then thoroughly mixes with charge 10, rises through charge 10, and eventually exits container 9 through stream 22. Suitable inert gasses for sparging through the polymerizable composition include those gasses which are inert, or substantially inert, to the ingredients of the polymerizable composition, and which do not materially interfere with the polymerization of the composition. Preferred gasses include argon and helium. An even more preferred gas is nitrogen.

Many types of devices are available which are suitable for sparging inert gas through the polymerizable composition, including several units available from Fisher Scientific, Kontes, and Coming Glass. For smaller applications, the coarse and extra coarse fritted gas dispersion tubes available from Fisher Scientific, having an 8 mm. I.D., are especially preferred, with the extra coarse dispersion tube being most preferred. Processes that use these tubes can readily be scaled up to large scale commercial applications. In some applications it may even be best to use more than one dispersion tube. In addition, other types of sparging units are suitable, such as the fritted cylindrical sealing tube also available from Fisher Scientific. This tubular unit has a centered, sealed in, fritted disk, and is available in fine, medium, coarse, or extra coarse porosity, any of which are suitable for practicing the invention. For smaller applications, the 13 mm. O.D., 25 mm. O.D., and 35 mm. O.D. tubes are all suitable. This type of unit may similarly be readily scaled up to large scale commercial applications. Other suitable gas dispersion methods and devices are, of course, known in the art.

Using the extra coarse fritted gas dispersion tubes available from Fisher Scientific, inert gas is preferably supplied to 200 ml. of a polymerizable composition in a container having an inside diameter of 4 inches at from about 0.5 to about 10 psi, even more preferably at from 0.75 to about 5 psi, and still even more preferably at from about 1 to about 3 psi. In another embodiment, using the coarse fritted gas dispersion tubes available from Fisher Scientific, inert gas is preferably supplied to a container of 200 ml. of polymerizable composition having an inside diameter of four inches at from about 0.5 to about 10 psi, even more preferably at from about 0.75 to about 5 psi, and still even more preferably at from about 1 to about 3 psi.

If the polymerizable composition contains a solvent, very effective oxygen removal can be accomplished by contacting the inert gas with the polymerizable composition, by methods such as sparging or bubbling, at a rate and for a period of time during which a de minimis amount of the solvent volatilizes. In order to minimize evaporation of solvent sparging is preferably carried out with minimal turbulence or agitation of the polymerizable composition. Sparging preferably is also carried out at a gaseous flow rate that thoroughly dissipates finely divided bubbles through the polymerizable composition. In a preferred embodiment inert gas is sparged through charge 10 from about 1 to about 30 minutes, more preferably from about 3 to about 10 minutes, and still even more preferably from about 5 to about 8 minutes.

Very effective oxygen removal can be accomplished by sparging an inert gas through the polymerizable composition according to this invention. In a preferred embodiment the deoxygenating step removes oxygen to below 500 ppm. In an even more preferred embodiment the deoxygenating step removes oxygen to below 200 ppm, and an even further preferred embodiment removes oxygen to below 100 ppm. Still even further embodiments remove oxygen to below 20, 10, and even 5 ppm. In preferred applications, the degree of oxygen removal refers to the amount of oxygen that must be removed to remove the excessive oxygen content from the composition.

After the sparging is complete the polymerizable composition is usually saturated with inert gas, and the composition remains saturated with inert gas through polymerization into an ophthalmic lens. The composition may, however, lose some inert gas content through subsequent processing steps such as pumping and dose injection into molds. Compositions that have lost some inert gas content through such processing steps are still considered to be substantially saturated with inert gas. Lenses obtained from compositions that may have lost some inert gas content to such subsequent processing, and which may have lost some inert gas content during the polymerization, are similarly still within the scope of this invention, and are considered to be substantially saturated with inert gas.

Figure 2:
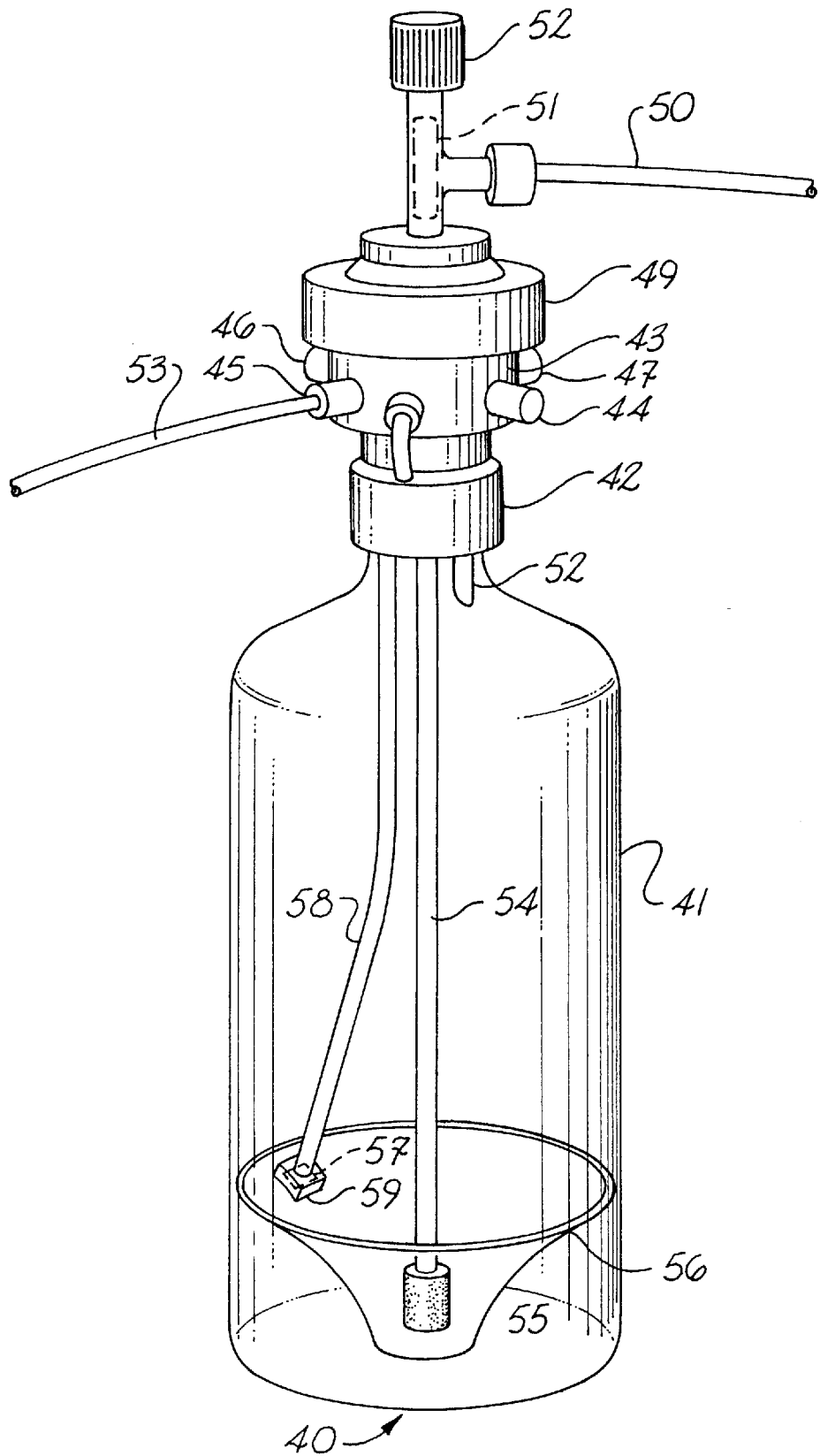
FIG. 2 is a perspective view of a particular unit for deoxygenating an ophthalmic lens polymerizable composition.

A preferred deoxygenating unit 40 is disclosed in FIG. 2. Unit 40 shown in FIG. 2 comprises a substantially enclosed body 41 sealed by a cap 42. A valve unit 43 comprising a series of valves 44–48 facilitates ingress and egress of polymerizable composition and sparging gas into and from body 41. A valve cap 49, through which polymerizable composition enters valve unit 43, encloses valve unit 43.

In operation a vacuum is drawn through pump valve 44, which draws polymerizable composition through line 50 into unit 40, and immediately through filter assembly 51. When incorporated into the process shown in FIG. 1, pump valve 44 draws polymerizable composition directly from line 4 into unit 40. A flow regulating valve 52 may be adjusted to regulate the flow of polymerizable composition into unit 40. After it has been filtered the polymerizable composition flows via gravimetric forces through valve unit 43 and out of exit portal 52 into body 41.

When the body 41 contains a sufficient charge of polymerizable composition it is deoxygenated by contacting the polymerizable composition with a suitable inert gas. Sparge valve 45 is adjusted to regulate the flow of pressurized inert gas through line 53 into valve unit 43. Pressurized inert gas is delivered to the charge of polymerizable composition through a fritted gas dispersion tube 54 that extends to and discharges inert gas at the bottom of body 41 through a porous frit 55 at one end of the tube 54. Porous frit 55 preferably comprises numerous pores to permit the discharge and uniform dispersion of finely divided bubbles into the charge of polymerizable composition. A conical bottom 56 for body 41 is especially effective for thoroughly and evenly dispersing the bubbles throughout the composition. In a particular embodiment deoxygenating unit 40 is fitted with a coarse or extra coarse 8 mm i.d. fritted gas dispersion tube available from Fisher Scientific. In a more preferred embodiment the unit 40 is fitted with the extra coarse 8 mm. i.d. fritted gas dispersion tube available from Fisher Scientific.

The bubbles travel through the composition and effectively displace dissolved gasses in the composition, especially oxygen, with inert gas. Gas that exits the polymerizable composition initially recombines above the polymerizable composition within body 41, before exiting unit 40 through gas discharge valve 46.

Monitors may optionally be integrated with deoxygenating unit 40 to monitor the level of oxygen remaining in the polymerizable composition during sparging, or to monitor the level of oxygen in the gas emitted through gas discharge valve 46, to ensure that the polymerizable composition is adequately deoxygenated before being removed from the deoxygenating unit. The deoxygenated polymerizable composition is removed from body 41, at entry 57, through tube 58. Entry 58 is optionally fitted with a filter 59 to remove entrained bubbles from the polymerizable composition. The deoxygenated polymerizable composition is preferably drawn from body 41 by a pump that is integrally connected through valve 47 to tube 58. Valve unit 43 is optionally fitted with a recirculation valve 48 that permits excess polymerizable composition to be recirculated directly into body 41 while maintaining the inert gas sparged environment. When deoxygenating unit 40 is integrated into the process shown in FIG. 1, line 11 is attached to valve 47.

As shown in FIG. 1, after the polymerizable composition has been sufficiently deoxygenated, all or part of it is conveyed to one or more ophthalmic lens mold units 17A–17E. In the process disclosed in FIG. 1 the deoxygenated polymerizable composition is first pumped by pump 12 from deoxygenating unit 30 into a reservoir 13 that is isolated from ambient gasses, and may preferably be backfilled with an inert gas. In some applications the composition may be agitated while in the reservoir to ensure adequate mixing, and to prevent phase separation. As needed, composition from the reservoir is drawn through line 14 into dispensing unit 15, through a pump that is integrated in dispensing unit 15. The dispensing unit dispenses carefully metered quantities of polymerizable composition through a plurality of lines 16A–16E into a mold assembly 17 comprising a plurality of mold cavities 17A–17E. The dispensing unit is preferably of the type having a valveless ceramic positive displacement dispense head combined with a stepping motor control, such as one of the precision liquid metering and dispensing systems that are commercially available from Ivek Corporation of North Springfield, Vt.

After the composition has been dispensed into a lens mold cavity, the mold is sealed and polymerization is initiated. Various lens mold designs are known that are suitable for practicing the invention. The composition of the lens mold with which the polymerizable comes into contact should preferably, however, be made from an inert composition. Polypropylene is an especially suitable composition for the mold. Suitable mold assemblies are disclosed, for example, in U.S. Pat. Nos. 5,658,602, 4,153,349, and 4,640,489, the disclosures from which being hereby incorporated by reference. The lens may optionally be produced in a spin casting mold such as the one disclosed in U.S. Pat. No. 5,260,001, the disclosure from which being hereby incorporated by reference. In addition, the molded lens may subsequently be lathed to produce a final lens.

Polymerization of the composition may be initiated by any means known to workers skilled in the art, and is optionally initiated with a photoinitiator to carry out photopolymerization. The photopolymerization can be initiated by actinic radiation, for example light, in particular UV light having a suitable wavelength. After the polymeric lens has been formed, the ophthalmic lens is removed from the mold by, for example, solvent swelling and other methods known to workers skilled in the art.

The polymerization is preferably carried out in an environment that has little oxygen. Suitable gases in which the polymerization may be conducted include, without limitation, nitrogen, helium, argon, and carbon dioxide, with nitrogen being particularly preferred. Thus, in a preferred embodiment, the polymerization occurs in an atmosphere having less than about 500 ppm oxygen. More preferably, the atmosphere surrounding the polymerizable composition contains less than about 200 ppm oxygen. Even more preferably, the surrounding atmosphere contains less than about 100 ppm oxygen, while the most preferred oxygen content is less than about 20 ppm.

It is also generally preferred to deoxygenate the lens molds, and to rigorously remove oxygen from the molding environment. Such removal is not always required, however, particularly if molds having a low oxygen permeability are used, such as polypropylene molds. In order to degas the lens molds, a preferred technique is to store the lens molds in an environment having no oxygen, or substantially no oxygen, for a sufficient period of time to achieve substantial equilibration. Preferably the lens molds are stored in an inert substantially oxygen-free atmosphere, e.g., nitrogen or carbon dioxide, prior to use. A preferred method of degassing molds is to subject the mold halves to an inert atmosphere having an oxygen concentration of less than 100 ppm for a period of at least 4 hours. A more preferred method involves exposing the mold halves to an inert atmosphere having an oxygen concentration of less than 50 ppm for a period of at least 6 hours. In an even more preferred method, the lens mold halves are exposed to an inert atmosphere having an oxygen concentration of less than 20 ppm for a period of at least 8 hours.

In another embodiment of the invention the manufacturing process is carried out by inhibiting the departure of volatile solvent from the polymerizable composition during sparging. In a particular embodiment, the volatilize solvent is inhibited from departing by passing the inert gas, after it has bubbled through the polymerizable composition, through a selectively permeable membrane, said membrane being permeable or substantially permeable to the inert gas and oxygen, and impermeable or substantially impermeable to volatilized solvent. By substantially permeable and impermeable is meant that degree of permeation which allows sufficient nitrogen and oxygen to escape the inert gas sparging system in order to obtain an acceptable ophthalmic lens upon polymerization, but which prevents more than a de minimis loss of volatile component. In another embodiment solvent that has evaporated from the polymerizable composition is condensed during or after sparging, and returned to the polymerizable composition before polymerization is initiated. The invention can also be practiced by pulling a vacuum on the composition in order to remove entrained bubbles before polymerization. In a preferred embodiment, however, such a vacuum step is omitted.

The compounds of the invention may be readily synthesized using techniques generally known to synthetic organic chemists. Suitable experimental methods for making and deriving ophthalmic lens compositions, and many of the ingredients of such compositions are described, for example, in the references cited in the Background section hereinabove, the disclosures of which are hereby incorporated by reference for their general teachings and for their synthesis teachings. Methods for making specific and preferred compositions of the present invention, and for carrying out the process of the invention, are described in detail in Examples 2 and 4 below.

Moreover, it will be apparent to workers of ordinary skill in the art that various modifications and variations can be made in the present invention without departing from the scope or spirit of the invention. For example, the various steps of the invention can be carried out either continuously or batch-wise, or a modified approach can be followed in which one or more of the steps is performed continuously and one or more of the steps is performed batchwise. Moreover, the polymerizable composition need not be prepared all at once, and the components of the polymerizable composition can be separately deoxygenated, or admixed with the other components of the polymerizable composition at any stage during the process, as long as the composition is sufficiently filtered and deoxygenated before polymerization is initiated.

EXPERIMENTAL

The following examples are put forth so as to provide workers of ordinary skill in the art with a complete disclosure and description of how the methods claimed herein are performed and evaluated, and are intended to be purely exemplary of the invention and not to limit the scope of what is regarded as the invention. Efforts have been made to ensure accuracy with respect to numbers (e.g., amounts, temperature, etc.) but some errors and deviations should be taken into account. Unless indicated otherwise, parts are parts by weight, temperature is in °C. or is at room temperature, and pressure is at or near atmospheric.

The polymerizable composition used in Examples 1 and 2 was prepared by admixing 50 parts by weight of an oxygen permeability enhancing prepolymer (a polydimethyl siloxane), 30 parts by weight of a hydrophilic enhancing prepolymer (dimethylacrylamide), 20 parts by weight TRIS, 33.3 parts by weight solvent (ethanol), and 0.5 parts by weight photoinitiator (Darocur). The composition was split equally between two containers, and the contents of each of the containers were subjected to one mold run.

EXAMPLE 1

Degassing Comparative Example

The contents of the first container were degassed using the in-line porous tubing/vacuum method known in the prior art, employing a high efficiency three channel Gastorre unit. The unit was made from Teflon tubing, and had a total void volume of 36 ml. (12 ml. per channel). From about 4 to about 6 ml. of composition were degassed per minute.

EXAMPLE 2

Deoxygenation By The Process Of The Invention

The contents of the second container were deoxygenated according to the process of this invention. A glass dispersion tube (8 mm i.d.) having a porous frit (extra course), obtained from Fisher Scientific, was inserted into the formulation, and nitrogen was bubbled through the composition at about 2 psi for about 10 min. The flow rate was adjusted to obtain substantially even penetration of the bubbles throughout the composition, while maintaining a smooth and laminar flow of bubbles. A breathable film designed to prevent permeation of water vapor, a/k/a parafilm made by American National Can, was wrapped around the formulation container opening to minimize solvent loss. After deoxygenating the container was capped and carried to the oxygen sensor.

The beginning and ending oxygen levels were recorded in ppm for both deoxygenating methods. Table 1 sets forth the results.

TABLE 1

Oxygen Sensor Readings

| Deoxygenating method | Estimated* ppm before deoxygenating | Average** ppm deoxygenating % Deoxygenation |
|---|---|---|
| In-line (Gastorre) | 46 | 4.424 |
| | | 90.38 |
| Nitrogen bubbling | 46 | 4.6175 |
| | | 89.96 |

Legend for TABLE 1
*Based upon experience with like monomers.
**Average of ppm at entrance to oxygen sensor and exit of oxygen sensor.

The deoxygenated formulations from examples 1 and 2 were also analyzed for % solids to determine the amount of solvent lost through evaporation. A 2 ml sample of each deoxygenated composition was injected into a gas chromatography unit that compared the retention time to a control sample. Regression analyses were performed and the % solids calculated. The known amounts were subtracted from 100 because the macromer amount could not be determined directly. The results for the two samples are listed in Table 2. The control amounts are listed in parenthesis in the column headings.

TABLE 2

Solvent Loss

| | % DMA (30 parts) | % TRIS (20 parts) | % Ethanol (33.33 parts) | % Darocur (0.5 parts) |
|---|---|---|---|---|
| Example 1 in-line | 29.63 ± 0.04 | 19.42 ± 0.14 | 33.02 ± 0.18 | 0.50 ± 0.01 |
| Example 2 nitrogen bubbling | 30.08 ± 0.05 | 19.93 ± 0.06 | 32.73 ± 0.15 | 0.50 ± 0.01 |

EXAMPLE 3

Comparative Degassing Process

According to U.S. Pat. No. 5,435,943, 8.5 ml/min of monomer containing excessive nitrogen (17 ppm) was deoxygenated, through 60 meters of porous silicon tubing (¼" i.d.), under a 4 torr vacuum, to obtain a monomer having a concentration of 0.58 ppm. Table 3 compares the oxygen removal efficiency of the method in U.S. Pat. No. 5,435,943, with the removal efficiency achieved by the process of this invention in Example 2.

TABLE 3

Composition Processing Rates

Deoxygenating
Method
Rate (ml
composition)/(liter
Example 2
(Nitrogen Bubbling)
100
Example 3
U.S. Pat. No. 5,435,943)
4.5

As shown in Table 3, the nitrogen bubbling of this invention deoxygenated the polymerizable composition at 22.4 times the rate of deoxygenation achieved in U.S. Pat. No. 5,435,943.

EXAMPLE 4

Molding Of Lenses From Deoxygenated Compositions

The deoxygenated compositions of examples 1 and 2 were subsequently molded by injecting 0.072 ml. of each of the compositions into 400 lens molds. The compositions were injected with a precision dose injection pump. The lens molds were made of polypropylene. Polymerization was initiated by application of UV light.

All lenses from these examples were within quality control specifications. The results from the two compositions are listed in Table 4 below. The specifications are in parenthesis in the column headings.

TABLE 4

Comparative Lens Specifications

| | Dk (95 ± 10) | IP (>1.5) | O.D./B.C. | Modulus (1.2 ± 0.3) | %NVE (<7/5)* | % wat (23.5 ± 2) |
|---|---|---|---|---|---|---|
| Example 1 Composition | 97 ± 5 | 1.625 ± 0.034 | 13.997/ 8.784 | 1.37 ± 0.11 | 6.57 ± 0.127 | 24.4 |
| Example 2 Composition | 103 ± 6 | 1.709 ± 0.136 | 13.985/ 8.750 | 1.41 ± 0.24 | 6.28 ± 0.141 | 23.6 |

Legend to TABLE 4
Dk - Oxygen Flux measured in barrers/mm (i.e., [(cc oxygen)/cm$^2$] × [sec/mm Hg] × 10$^{-10}$.
IP - Ion Permeability Coefficient in cm$^2$/sec × 10$^4$.
O.D./B.C. - Outer diameter in mm/base curve in mm.
Modulus - Modulus of Elasticity
NVE - Non-Volatile Extractables
*NVE specification is based upon historical data.

Throughout this application, various publications are referenced. The disclosures of these publications in their entireties are hereby incorporated by reference into this application in order to more fully describe the state of the art to which this invention pertains. Moreover, other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making an ophthalmic lens comprising the steps of:
   a. preparing a polymerizable composition having excessive oxygen content;
   b. contacting the polymerizable composition with a gas that is inert or substantially inert to the polymerizable composition by sparging or bubbling, and deoxygenating or partially deoxygenating the polymerizable composition;
   c. conveying all or part of the polymerizable composition to an ophthalmic lens mold; and
   d. polymerizing all or part of the polymerizable composition to obtain a polymeric ophthalmic lens.

2. The method of claim 1 wherein at least one of the steps is performed continuously.

3. The method of claim 1 wherein at least one of the steps is performed batch-wise.

4. The method of claim 1 wherein the inert gas is nitrogen, argon, or helium.

5. The method of claim 1 further comprising the step of removing the ophthalmic lens from the mold.

6. The method of claim 1 wherein the polymerizable composition comprises a hydrophilic enhancing prepolymer.

7. The method of claim 1 wherein the polymerizable composition comprises an acrylate, a methacrylate, a poly (alkylene glycol), a N-vinyl pyrrolidone, a residue thereof, or a mixture thereof.

8. The method of claim 1 wherein the polymerizable composition comprises 2-hydroxyethyl methacrylate or a residue thereof.

9. The method of claim 1 wherein the polymerizable composition comprises an oxygen permeability enhancing prepolymer.

10. The method of claim 1 wherein the polymerizable composition comprises a silicon residue, a fluorine residue, an alkyne group, or a mixture thereof.

11. The method of claim 1 wherein the polymerizable composition comprises a dialkylsiloxane group or residue.

12. The method of claim 1 wherein the polymerizable composition comprises a hydrophilic enhancing prepolymer and an oxygen permeability enhancing prepolymer.

13. The method of claim 1 wherein the polymerizable composition comprises TRIS.

14. The method of claim 1 wherein the polymerizable composition comprises from about 40 to about 80 parts by weight one or more oxygen permeability enhancing prepolymers, and from about 10 to about 40 parts by weight one or more hydrophilic enhancing prepolymers.

15. The method of claim 1 wherein the polymerizable composition comprises from about 40 to about 80 parts by weight one or more oxygen permeability enhancing prepolymers, from about 10 to about 40 parts by weight one or more hydrophilic enhancing prepolymers, and from about 10 to about 20 weight percent TRIS.

16. The method of claim 1 wherein the polymerizable composition comprises a volatile component.

17. The method of claim 1 wherein the polymerizable composition comprises a solvent.

18. The method of claim 1 wherein the polymerizable composition comprises from about 10 to about 40 wt.% of a volatile component.

19. The method of claim 1 wherein the polymerizable composition comprises a volatile component, and wherein the weight percentage of the volatile component in the composition can vary by up to 5% without materially affecting the ophthalmic lens.

20. The method of claim 1 wherein the polymerizable composition comprises a volatile component that has a vapor pressure in excess of about 40 mm Hg.

21. The method of claim 1 wherein the polymerizable composition has a surface tension below about 35 dynes/cm.

22. The method of claim 1 wherein the polymerizable composition has a viscosity below about 75 cps.

23. The method of claim 16 wherein the inert gas is contacted with the polymerizable composition for a period of time during which none or a de minimis amount of the volatile component volatilizes.

24. The method of claim 1 wherein the contacting is performed from about 3 to about 10 minutes.

25. The method of claim 1 wherein the gas contacting removes oxygen from the polymerizable composition to a level below about 10 ppm.

26. The method of claim 1 wherein the gas is contacted with the polymerizable composition at a pressure of from about 0.5 to about 10 psi.

27. The method of claim 1 wherein the gas is contacted with the polymerizable composition at a pressure of from about 0.75 to about 5 psi.

28. The method of claim 16 further comprising the step of inhibiting the departure of the volatile component from the polymerizable composition during sparging or bubbling.

29. The method of claim 28 wherein the volatile component is inhibited from departing by passing the inert gas, after it has contacted with the polymerizable composition, through a selectively permeable membrane, said membrane being permeable or substantially permeable to the inert gas and oxygen, and impermeable or substantially impermeable to the volatile component that has volatilized.

30. The method of claim 16 further comprising the step of condensing volatile component that has volatilized from the polymerizable composition during or after contact, and returning the condensed component to the polymerizable composition.

* * * * *